(12) United States Patent
Colberg et al.

(10) Patent No.: US 6,232,500 B1
(45) Date of Patent: May 15, 2001

(54) PROCESS FOR PREPARING A KETIMINE

(75) Inventors: Juan Carlos Colberg, Norwich; David Michael Pfisterer; Geraldine Patricia Taber, both of Mystic, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/380,562
(22) PCT Filed: Oct. 15, 1998
(86) PCT No.: PCT/IB98/01619
  § 371 Date: Sep. 2, 1999
  § 102(e) Date: Sep. 2, 1999
(87) PCT Pub. No.: WO99/36394
  PCT Pub. Date: Jul. 22, 1999

Related U.S. Application Data
(60) Provisional application No. 60/071,600, filed on Jan. 16, 1998.

(51) Int. Cl.[7] .................................................. C07C 249/02
(52) U.S. Cl. ............................................. 564/271; 564/270
(58) Field of Search ................................... 564/270, 272; 514/676

(56) References Cited

U.S. PATENT DOCUMENTS

| 4,536,518 | 8/1985 | Welch et al. | 514/647 |
|---|---|---|---|
| 4,855,500 | 8/1989 | Spavins | 564/270 |

FOREIGN PATENT DOCUMENTS 9957093  11/1999  (WO).

OTHER PUBLICATIONS

CA: 102:220171 abs of J Org Chem ab of Botta 50(11) pp 1916–1919, 1985.*

Tetrahedron vol. 48 No. 47 by Quallich et al pp 10239–10248, 1992.*

* cited by examiner

*Primary Examiner*—Jean F. Vollano
(74) *Attorney, Agent, or Firm*—Peter C. Richardson; Paul H. Ginsburg; Alan L. Koller

(57) ABSTRACT

This invention relates to a novel improved process for preparation of N-[4-(3,4-dichlorophenyl)-3,4-dihydro-1(2H)-naphthalenylidene]methanamine from 4-(3,4-dichloro-phenyl)-3,4-dihydro-1(2H)-naphthalenone and monomethylamine.

30 Claims, No Drawings

PROCESS FOR PREPARING A KETIMINE

This application is the U.S. national stage of PCT/IB98/01619, filed Oct. 15, 1998, which claims priority from U.S. Provisional application Serial No. 60/071,600, filed Jan. 16, 1998.

BACKGROUND OF THE INVENTION

This invention relates to a new, simplified method of preparing a known ketimine compound. Specifically, it is concerned with the synthesis of N-[4-(3,4-dichlorophenyl)-3,4-dihydro-1(2H)-naphthalenylidene-]methanamine, a critical intermediate in the production of cis-(1S)(4S)-N-methyl-4(3,4-dichlorophenyl)-1,2,3,4-tetrahydro-1-naphthaleneamine (sertraline). Sertraline hydrochloride is the active ingredient in the antidepressant Zoloft.

The most widely used route to date for the commercial preparation of N-[4-(3,4-dichlorophenyl)-3,4-dihydro-1 (2H)-naphthalenylidene]methanamine, leading to cis-(1S) (4S)-N-methyl4(3,4-dichlorophenyl)-1,2,3,4-tetrahydro-1-naphthaleneamine (sertraline), involves a condensation reaction of 4-(3,4-dichlorophenyl)-3,4-dihydro-1(2H)-naphthalenone with monomethylamine, which is catalyzed by titanium tetrachloride, as described by W. R. Welch, Jr. et al. in U.S. Pat. No. 4,536,518 and in Journal of Medicinal Chemistry, Vol. 27, No. 11, p 1508, 1984. However, the safety concerns (due to extreme reactivity with water) and hazardous by-products (namely, titanium dioxide monomethylamine hydrochloride) associated with use of titanium tetrachloride, have prompted evaluation of alternative dehydrating agents that would eliminate the formation of hazardous by-products. The advantages associated with elimination of solid by-product formation include not only improved safety, but also improved productivity associated with elimination of the need for filtration of the by-product from the reaction medium. The process of filtering titanium dioxide monomethylamine hydrochloride on common commercially available isolation devices is very time consuming.

An alternative route to N-[4-(3,4-dichlorophenyl)-3,4-dihydro-1(2H)-naphthalenyl-idene-]methanamine is described in U.S. Pat. No. 4,855,500 to J. C. Spavins, wherein the dehydration characteristics of appropriate mesh molecular sieves are employed to promote the condensation reaction between 4-(3,4-dichlorophenyl)-3,4-dihydro-1 (2H)-naphthalenone and monomethylamine. The appropriate type molecular sieves (specifically, those having a pore size of about 3 Angstroms) are contacted in-situ with the mixture of 4-(3,4-dichlorophenyl)-3,4-dihydro-1(2H)-naphthalenone and monomethylamine, and adsorb the water formed from the condensation reaction. Once the desired condensation reaction is essentially complete, forming N-[4-(3,4-dichlorophenyl)-3,4-dihydro-1(2H)-naphthalenylidene-]methanamine, the water saturated molecular sieves must be removed from the product containing solution by filtration prior to isolation of the ketimine product. Furthermore, used sieves must typically be regenerated if they are to be reused.

The process of this invention provides a novel and useful synthetic route to N-[4-(3,4-dichlorophenyl)-3,4-dihydro-1 (2H)-naphthalenylidene-]methanamine, known to be a useful intermediate in the synthesis of sertraline. This novel route involves a condensation reaction between 4-(3,4-dichlorophenyl)-3,4-dihydro-1(2H)-naphthalenone and monomethylamine in a solvent such as an alkanol or a mixture of two or more alkanols. The nature of the solvent and the solubility of N-[4-(3,4-dichlorophenyl)-3,4-dihydro-1 (2H)-naphthalenylidene-]methanamine in the solvent are such that reaction equilibrium is favorably enhanced towards the ketimine product, namely N-[4-(3,4-dichlorophenyl)-3,4-dihydro-1(2H)-naphthalenylidene-] methanamine. The desired ketimine is thus produced in acceptable purity and high yield without requiring the addition of a heterogeneous catalyst, such as, for example, molecular sieves. This novel, one step approach to the synthesis of N-[4-(3,4-dichlorophenyl)-3,4-dihydro-1(2H)-naphthalenylidene-]methanamine from 4-(3,4-dichlorophenyl)-3,4-dihydro-1(2H)-naphthalenone therefore avoids the above described disadvantages associated with the titanium tetrachloride route. Moreover, the need for addition of a dehydration agent (es, titanium tetrachloride or molecular sieves or another such dehydration promoting additive) is eliminated, as is the associated need for removal of by-products or spent sieves from the completed reaction mixture.

SUMMARY OF THE INVENTION

This invention relates to a process for preparing N-[4-(3,4-dichlorophenyl)-3,4-dihydro-1(2H)-napthalenylidene] methaneamine, depicted below,

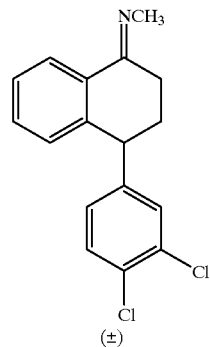

II comprising reacting 4-(3,4-dichlorophenyl)-3,4-dihydro-1 (2H)-napthalenone, depicted below and also referred to herein as "tetralone",

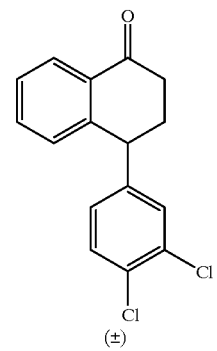

I with monomethylamine in an alcohol solvent selected from primary, secondary and tertiary straight or branched ($C_1$–$C_6$) alkanols, and other alcohols having a boiling point, under reaction conditions, that is greater than about 55° C., and in which monomethylamine is soluble.

Examples of suitable solvents for use in the processes of this invention are benzyl alcohol, phenol, ethanol, n-propanol, isopropanol, t-butanol, isobutanol, n-butanol and methanol.

Preferred solvents for use in the processes of this invention are alcohols, as defined above, having a vapor pressure that is about 1 atmosphere or lower under reaction conditions.

A more specific embodiment of this invention relates to the process described above, wherein the ketimine product of formula II that is formed in such process is hydrogenated to form a mixture of racemic cis sertraline and racemic trans sertraline.

The terms "sertraline" and "cis (+) sertraline", as used herein, both refer to cis-(1S)(4S)-N-methyl-4-(3,4-dichlorophenyl)-1,2,3,4-tetrahydro-1-naphthaleneamine.

The term "trans (+) sertraline", as used herein, refers to trans-(1R) (4S)-N-methyl-4-(3,4-dichlorophenyl)-1,2,3,4-tetrahydro-1-naphthaleneamine.

The term "cis (−) sertraline", as used herein, refers to cis-(1R) (4R)-N-methyl-4-(3,4-dichlorophenyl)-1,2,3,4-tetrahydro-1-naphthaleneamine.

The term "trans (−) sertraline", as used herein, refers to trans-(1S) (4R)-N-methyl-4-(3,4-dichlorophenyl)-1,2,3,4-tetrahydro-1-naphthaleneamine.

The term "racemic cis sertraline", as used herein, refers to an optically inactive mixture of cis (+) sertraline and cis (−) sertraline.

The term "racemic trans sertraline", as used herein, refers to an optically inactive mixture of trans (+) sertraline and trans (−) sertraline.

The term "racemic sertraline", as used herein, refers to an optically inactive mixture of racemic cis sertraline and racemic trans sertraline.

This invention also relates to a process for preparing the optically pure (+) enantiomer of N-[4-(3,4-dichlorophenyl)-3,4-dihydro-1(2H)-napthalenylidene]methaneamine, depicted below,

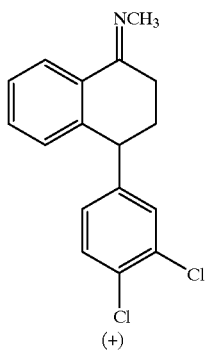

II' or an optically enriched (+) mixture of the (+) and (−) enantiomers of the same, respectively;

comprising reacting the optically pure (+) enantiomer of 4-(3,4-dichlorophenyl)-3,4-dihydro-1(2H)-napthalenone, depicted below,

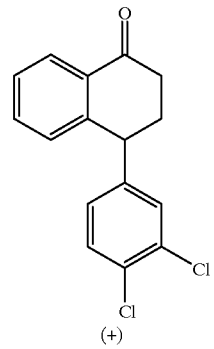

I' or an optically enriched (+) mixture of the (+) and (−) enantiomers of the same, respectively, with monomethylamine in an alcohol solvent selected from primary, secondary and tertiary straight or branched ($C_1$–$C_6$) alkanols, and other alcohols having a boiling point, under reaction conditions, that is greater than about 55° C., and in which monomethylamine is soluble.

A more specific embodiment of this invention relates to the process described immediately above, wherein the optically pure or optically enriched (+) ketimine product of formula II' that is formed in such process is hydrogenated to form an optically pure (+) mixture of cis (+) sertraline and trans (+) sertraline, or an optically enriched (+) mixture of cis (+) sertraline, trans (+) sertraline, cis (−) sertraline and trans (−) sertraline.

This invention also relates to a process for preparing a mixture of racemic cis sertraline and racemic trans sertraline, comprising reacting a compound of the formula I, as depicted above, with monomethylamine, hydrogen gas (i.e., under a hydrogen atmosphere) and a hydrogenation catalyst in a solvent selected from primary, secondary and tertiary straight or branched ($C_1$–$C_6$) alkanols, and other alcohols having a boiling point, under reaction conditions, that is greater than about 55° C., and in which monomethylamine is soluble.

This invention also relates to a process for preparing an optically pure (+) mixture of cis (+) sertraline and trans (+) sertraline, or an optically enriched (+) mixture of cis (+) sertraline, trans (+) sertraline, cis (−) sertraline and trans (−) sertraline, comprising reacting a compound of the formula I', as depicted above, with monomethylamine, hydrogen gas (i.e., under a hydrogen atmosphere) and a hydrogenation catalyst in a solvent selected from primary, secondary and tertiary straight or branched ($C_1$–$C_6$) alkanols, and other alcohols having a boiling point, under reaction conditions, that is greater than about 55° C., and in which monomethylamine is soluble.

Other more specific embodiments of this invention relate to the above processes, wherein the solvent is selected from phenol, benzyl alcohol, ethanol, n-propanol, isopropanol, n-butanol, t-butanol, isobutanol and methanol.

As used herein, the term ($C_1$–$C_6$)alkyl refers to straight chain, branched or cyclic saturated hydrocarbon radicals containing from 1–6 carbon atoms, and to saturated ($C_1$–$C_6$) hydrocarbon radicals containing both cyclic and straight chain or branched moieties.

DETAILED DESCRIPTION OF THE INVENTION
The process of this invention, as well as the use of the ketimine products of such processes in the synthesis of sertraline, are illustrated in the following schemes and described below.
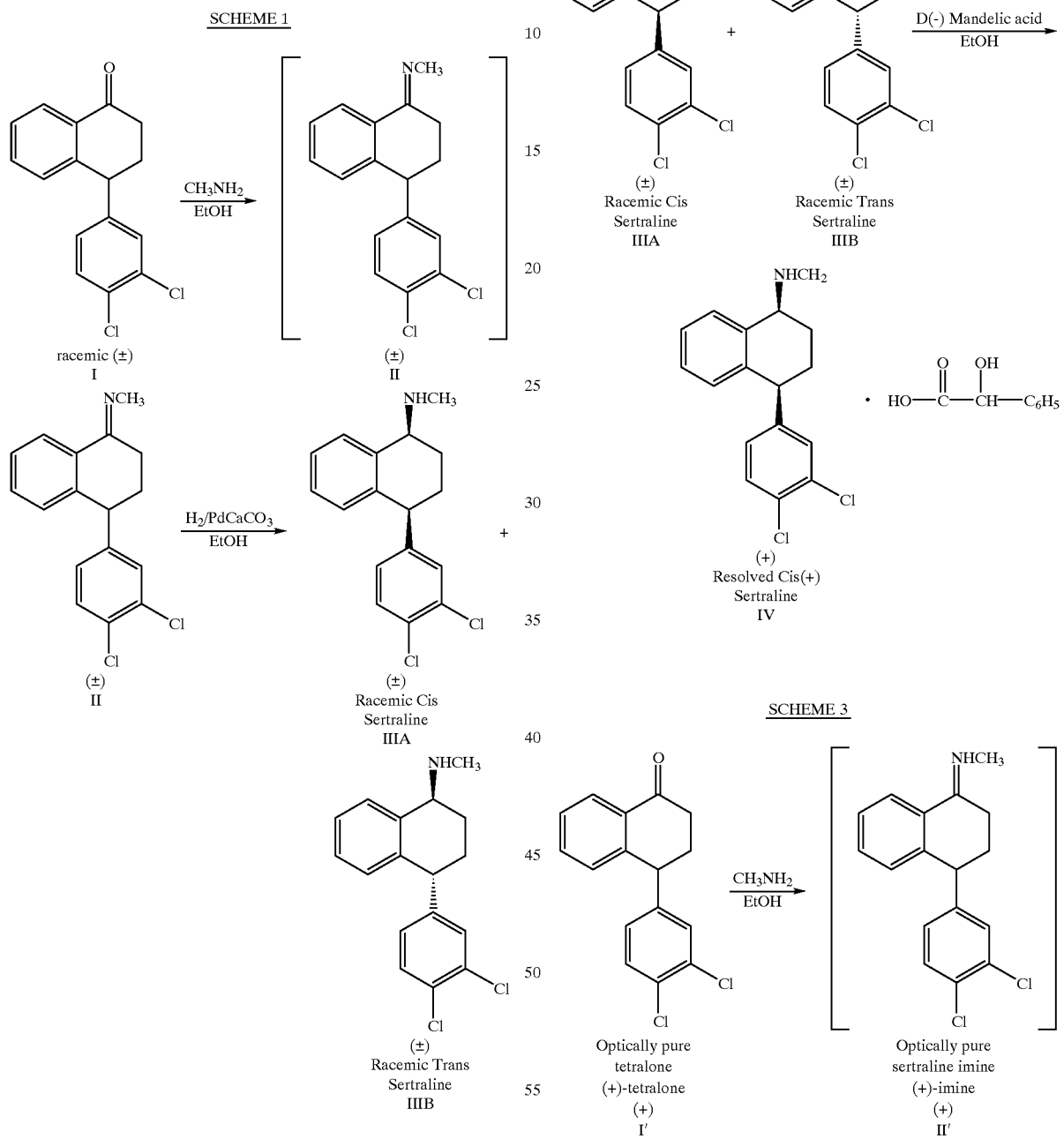

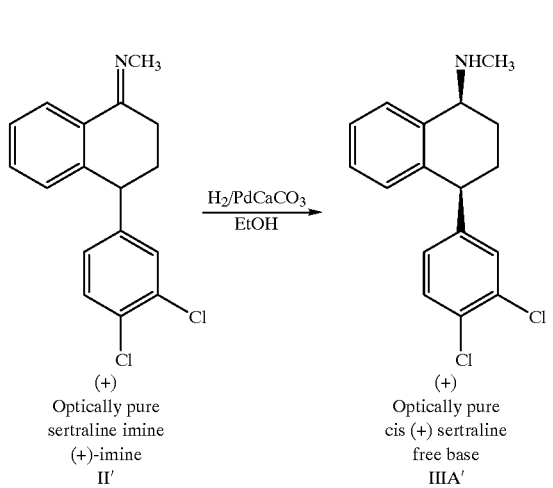
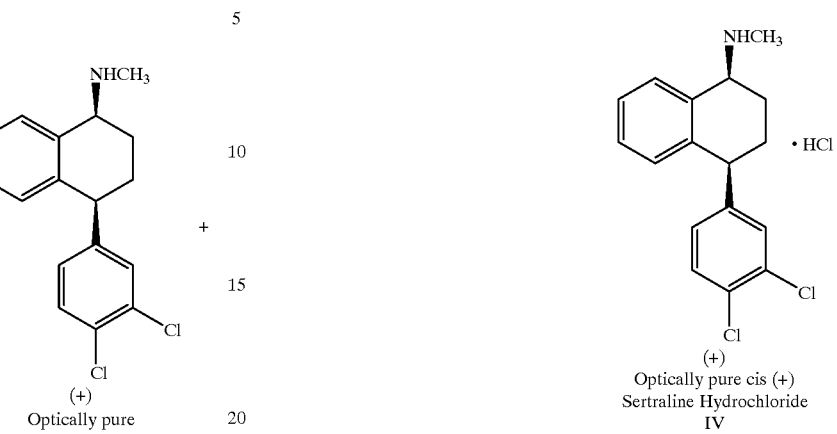
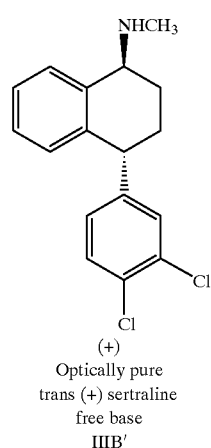
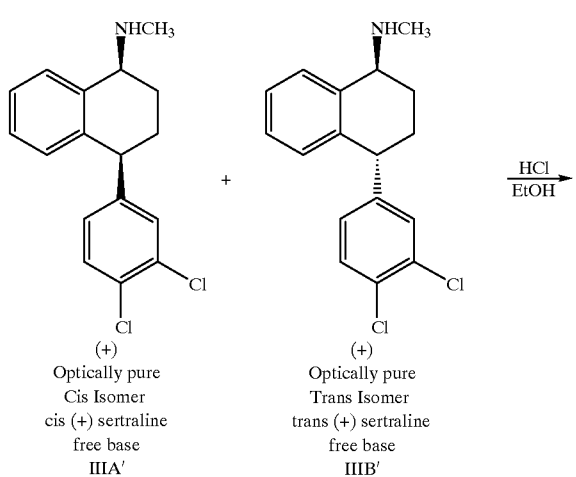

In accordance with the process of this invention, the reaction to form the ketimine is generally carried out preferably in a lower alkanol solvent. It is preferably carried out using an excess of monomethylamine with respect to 4-(3, 4-dichlorophenyl)-3,4-dihydro-1(2H)-naphthalenone. It is most preferably carried out using ethanol as the solvent and a range of between 2.5 and 9.5 moles of monomethyl amine per mole of 4-(3,4-dichlorophenyl)-3,4-dihydro-1(2H)-naphthalenone. This reaction can be carried out at temperatures ranging from about room temperature to about 120° C. It is preferably carried out at a temperature between about 40° C. and about 60° C. The preferred reaction pressure will depend on the mole ratio of monomethyl amine employed, as well as the vapor pressure of the alcohol solvent, and will typically be in the range of about atmospheric pressure to 60 psig. The reaction is most optimally performed in a pressure rated vessel, although atmospheric conditions have been successfully employed to achieve acceptable reaction completion. The reaction is continued under the conditions described above until such time as it is substantially complete, which is typically in the region of about six to about twenty hours.

Most preferred reaction promoting solvents for use in this application include primary, secondary or tertiary alcohols such as ethanol, methanol, isopropanol, n-butanol, t-Butanol, as well as aryl alcohols such as phenols, substituted phenols, benzyl alcohol, and substituted benzyl alcohols. Preferable characteristics of the above alcohol solvents in this connection include low vapor pressure as well as high monomethylamine solubility. It is also believed that the minimal solubility of the desired product (N-[4-(3,4-dichlorophenyl)-3,4-dihydro-1(2H)-naphthalenylidene-] methanamine) in such solvents favors an improved reaction rate, as well as more facile product isolation through filtration and optimal yield.

Dehydration agents, such as molecular sieves, while not required, may be employed externally to the medium distillates to improve the desired ketimine reaction yield and rate.

Upon completion of the ketimine reaction under the above specified conditions, the desired product, namely N-[4-(3,4-dichlorophenyl)-3,4-dihydro-1(2H)-naphthalenylidene]-methanamine, may be isolated in a simple manner by filtration, or via concentration and/or displacement of the solvent with another appropriate solvent such as hexane, followed by filtration of the solid ketimine product.

Alternatively, and preferably, the resulting alcohol ketimine mixture is processed directly forward, without isolation, to the next synthetic step in the production of sertraline, whereby catalytic hydrogenation of the ketimine to form a mixture of racemic cis and racemic trans sertraline (the next-stage intermediate in the synthesis of sertraline) is performed with the same alcohol as the solvent. The hydrogenation to racemic cis and racemic trans sertraline may be carried out successfully either after ketimine formation is complete, or concurrently with the ketimine formation, in a reductive amination manner. The reductive amination approach involves combining racemic 4-(3,4-dichlorophenyl)-3,4-dihydro-1(2H)-naphthalenone with monomethylamine (ideally 2.5 to 3.5 mole equivalents) and a suitable hydrogenation catalyst, such as Pd/CaCO$_3$ (typically up to about 20% w/w relative to the starting material), under a hydrogen atmosphere, in an alcohol solvent, as defined above, until hydrogen uptake ceases or the reaction is otherwise shown to be complete. This reaction is typically carried out at a temperature from about 20° C. to about 100° C., preferably from about 30° C. to about 70° C., at a pressure from about 20 psig to about 100 psig, preferably from about 20 psig to about 60 psig. Under these conditions, the racemic 4-(3,4-dichlorophenyl)-3,4-dihydro-1(2H)-naphthalenone is converted into racemic N-[4-(3,4-dichlorophenyl)-3,4-dihydro-1(2H)-napthalenylidene-]methanamine and immediately reduced to the desired mixture of racemic cis sertraline and racemic trans sertraline.

The preferred temperature range for the hydrogenation reaction is from about 20° C. to about 100° C., and the preferred range of hydrogen pressures is from about 0 psig to about 100 psig. The most preferable temperatures are within the range of about 20° C. to about 50° C., and the most preferable hydrogen pressures are within the range from about 10 psig to about 60 psig.

Preferable catalysts for the reduction or reductive amination described above include platinum, palladium and other precious metal promoters on supports such as carbon, graphite, calcium carbonate or other such supports, all of which are well known in the catalytic hydrogenation industry.

Following completion of the reduction reaction, a filtration is performed to remove process catalyst. Excess monomethylamine is removed via distillation and/or displacement of the original solvent with another suitable solvent such as an alternative alcohol, tetrahydrofuran, methyl ethyl ketone, or toluene.

The resulting solution of racemic N-methyl-4-(3,4-dichlorophenyl)-1,2,3,4-tetrahydro-1-naphthalenamine may be treated with an appropriate acid, and the desired cis-N-methyl-4-(3,4-dichlorophenyl)-1,2,3,4-tetrahydro-1-naphthalenamine salt isolated by filtration.

Alternatively, and most preferably, the solution of racemic N-methyl-4-(3,4-dichlorophenyl)-1,2,3,4-tetrahydro-1-naphthalenamine may be chirally resolved by combination with an appropriate optically pure acid, such as (D)(−)-mandelic acid, to afford the mandelate salt of cis (+) sertraline, which can then be isolated by filtration. The resolved salt can then be hydrolyzed to form the sertraline free base having the same stereochemistry, which can then be converted into other pharmaceutically acceptable salt forms of sertraline having the same stereochemistry, including the hydrochloride salt, using methods well known to those of skill in the art.

If, as illustrated in Scheme 3, the above process is carried out using optically pure (or optically enriched) (+) tetralone as the starting material and the reaction conditions described above, the reaction will yield the optically pure (or optically enriched) (+) sertraline imine of the formula II', which can then be converted, without requiring a separate resolution step, into the sertraline free base, which can then be converted into the desired hydrochloride salt or other salt of sertraline.

The 4-(3,4-dichlorophenyl)-3,4-dihydro-1(2H)-naphthalenone ketone, which is the starting material for the ketimine formation process of this invention, may be readily synthesized by those skilled in the art using common chemical reagents and conventional methods of organic synthesis, such as those outlined by W. M. Welch, Jr. et al. in U.S. Pat. No. 4,536,518 or the Journal of Medicinal Chemistry, Vol. 27, No. 11, p 1506, 1984.

As illustrated in Scheme 3, use of the optically pure tetralone as the starting material for the ketimine formation reaction eliminates the necessity of having to resolve the free base racemic sertraline later in the process, because both the ketimine formation reaction and the hydrogenation/reductive amination reactions described above proceed with preservation of stereochemistry.

The novel process of this invention provides a significantly simplified route to N-[4-(3,4-dichlorophenyl)-3,4-dihydro-1(2H)-naphthalenylidene-]methanamine from 4-(3,4-dichlorophenyl)-3,4-dihydro-1(2H)-naphthalenone. Furthermore, this novel route, described above, facilitates the ability to produce (1S-cis)-4-(3,4-dichlorophenol)-1,2,3,4-tetrahydro-N-methyl-1-naphthalenamine mandelate, the mandelate salt of sertraline, which can easily be converted into the sertraline free base and other pharmaceutically acceptable salts of sertraline, in a manner that eliminates several intermediate isolation steps. The process of this invention provides the above mentioned ketimine in pure form and good yield, with the significant advantage of eliminating dehydration catalyst related by-products such as titanium dioxide, monomethylamine hydrochloride, and spent molecular sieves as described above. The elimination of by-products specifically improves both process safety and economics. Titanium tetrachloride is expensive as well as hazardous. Also, the proper and safe treatment of process by-products is expensive. Furthermore, the process of this invention allows for processing the ketimine intermediate directly forward to the next two synthetic steps in the synthesis of sertraline, most ideally in a common solvent, thus eliminating the need for isolation of the ketimine intermediate and improving the overall economic viability of the commercial production of sertraline.

The following examples illustrate, but do not limit in scope, the novel process of this invention.

EXAMPLE 1

Sertraline Imine through Sertraline Mandelate Formation in Ethanol

Tetralone (63.6 g, 1 mol eq) is combined with ethanol (anhydrous, 2B, 250 mL) in a suitable pressure rated vessel equipped with agitation and hydrogen source. The mixture is cooled to 0° C. and monomethylamine (21.1 g, 3.1 mol eqs) added in a sub-surface manner. The mixture is warmed to 50–55° C. and stirred under these conditions for approximately 16 hours, or until >95% conversion to imine has been shown to have occurred by suitable analysis. The mixture is then cooled to 20–22° C., a palladium/calcium carbonate (Pd/CaCO$_3$) catalyst (1–2% w/w to tetralone) and decolorizing carbon (2–5% w/w to tetralone) are added and the mixture is pressurized to approximately 50 psig with hydrogen. The contents are warmed to between 25 and 40° C. to facilitate the rate of hydrogenation. The reaction is continued until hydrogen uptake ceases, or until the reaction mixture is shown to contain no greater than 3% total unreacted tetralone and imine. Upon completion, the mixture is cooled to less than 25° C. and the carbon and catalyst removed by filtration. Excess monomethylamine is then removed by vacuum distillation of ethanol, via displacement with fresh ethanol (2B, anhydrous). Once the level of residual monomethylamine is shown to be below 0.1% w/v, mandelic acid is added (30.0 g, 0.9 mol eqs) and the mixture heated to reflux. The desired mandelate salt of cis (+) sertraline is crystallized from the mixture by slow cooling to approximately 5° C. to control the selecting crystallization. The product is isolated by filtration and washed with chilled ethanol. Enantiomeric purity and overall purity can be enhanced by recrystallization from ethanol, while use of carbon in the recrystallization offers additional control of product color. Typical yield from tetralone to recrystallized mandelate is 38%, with respect to the weight of the racemic tetralone starting material.

EXAMPLE 2

Sertraline Imine through Sertraline Mandelate Formation in Methanol

Tetralone (63.6 g, 1 mol eq) is combined with methanol (250 mL) in a suitable pressure rated vessel equipped with agitation and hydrogen source. The mixture is cooled to 0° C. and monomethylamine (21.1 g, 3.1 mol eqs) added in a sub-surface manner. The mixture is warmed to 50–55° C. and stirred under these conditions for approximately 16 hours, or until >95% conversion to imine has been shown to have occurred by suitable analysis. The mixture is then cooled to 20–22° C., Pd/CaCO$_3$ catalyst (1–2% w/w to tetralone) and decolorizing carbon (2–5% w/w to tetralone) added and the mixture pressurized to approximately 50 psig with hydrogen. The contents are warmed to between 25 and 40° C. to facilitate the rate of hydrogenation. The reaction is continued until hydrogen uptake ceases, or until the reaction mixture is shown to contain no greater than 3% total unreacted tetralone and imine. Upon completion, the mixture is cooled to less than 25° C. and the carbon and catalyst removed by filtration. Excess monomethylamine is then removed by vacuum displacement of methanol, through displacement with fresh methanol. Once the level of residual monomethylamine is shown to be below 0.1% w/v, mandelic acid is added (30.0 g, 0.9 mol eqs) and the mixture heated to reflux. The desired mandelate salt of cis (+) sertraline crystallizes from the mixture by slow cooling to approximately –10° C. The product is isolated by filtration and washed with chilled methanol. Enantiomeric purity and overall purity can be enhanced by recrystallization from either methanol or ethanol, while use of carbon in the recrystallization offers additional control of product color. Typical yield from tetralone to recrystallized mandelate with methanol as solvent is 32%.

EXAMPLE 3

Imine Formation in Isopropyl Alcohol

Tetralone (165 g, 1 mol eq) is combined with isopropyl alcohol (700 mL) in a suitable pressure rated vessel and the mixture cooled to –5C. to –10° C. Monomethylamine (60.2 g, 3.4 mol eqs) is added and the mixture heated to 85–100° C. for 16 hours, whereupon 95% imine conversion was shown to have occurred. The mixture is then cooled to –15° C. for 24 hours, and the product isolated by filtration in approximately 92% yield and approximately 95% purity. As an alternative, in a related experiment, Pd/CaCO$_3$ catalyst and decolorizing carbon is added to the cooled reaction mixture, and the imine hydrogenated to racemic sertraline free base in a manner similar to that described above for ethanol and methanol series.

EXAMPLE 4

Reductive Amination to Form Racemic Sertraline Free Base In Ethanol

Tetralone (120 g, 1 mol eq) is combined with ethanol (2B, anhydrous, 600 mL) in a suitable pressure rated vessel, and the contents cooled to 0° C. Monomethylamine (43 g, 3.4 mol eqs) and Pd/CaCO$_3$ catalyst (3% w/w to tetralone) is added, and the vessel pressurized to 50 psig with hydrogen while warming to 50° C. The mixture was maintained under these conditions for approximately 10 hours, whereupon 92% cis plus trans racemic sertraline, approximately 4.5% tetralone, 2% imine and less than 1% dechlorinated side products are typically observed in the mixture. Catalyst is then removed by filtration, followed by vacuum distillation to remove excess monomethylamine. Mandelic acid (65.8 g, 0.9 mol eqs) is added, and the product isolated in similar yield and quality as per the above description for Sertraline Mandelate Formation in Ethanol (Example 1).

EXAMPLE 5

Sertraline Imine Formation in Propyl Alcohol

Tetralone (140 g, 1 mol eq) is combined with n-propyl alcohol (700 mL) in a suitable pressure rated vessel. The mixture is cooled to –5° C., and monomethylamine (100 g, 6.7 mol eq) added. The mixture is heated to 100° C., and stirred under these conditions for 12 hours. After this time, the mixture is cooled to –15° C. and the product isolated by filtration in 92% yield and >95% purity.

EXAMPLE 6

Sertraline Imine Through Racemic Sertraline Hydrochloride Formation in Ethanol

Tetralone (63.6 g, 1 mol eq) is combined with ethanol (anhydrous, 2B, 250 mL) in a suitable pressure rated vessel equipped with agitation and hydrogen source. The mixture is cooled to 0° C. and monomethylamine (21.1 g, 3.1 mole equivalents) added in a sub-surface manner. The mixture is warmed to 50–55° C. and stirred under these conditions for approximately 16 hours, or until >95% conversion to imine has been shown to have occurred by suitable analysis. The mixture is then cooled to 20–22° C., Pd/CaCO$_3$ catalyst (1–2% w/w to tetralone) and decolorizing carbon (2–5% w/w to tetralone) added and the mixture pressurized to approximately 50 psig with hydrogen. The contents are warmed to between 25 and 40° C. to facilitate the rate of hydrogenation. The reaction is continued until hydrogen uptake ceases, or until the reaction mixture is shown to contain no greater than 3% total unreacted tetralone and imine. Upon completion, the mixture is cooled to less than 25° C. and the carbon and catalyst removed by filtration. Excess monomethylamine is then removed by vacuum distillation of ethanol, via displacement with fresh ethanol (2B, anhydrous). Hydrochloric acid (35%, 21.5 g, 1 mole equivalent) is added and racemic sertraline hydrochloride isolated by filtration. Overall purity can be enhanced by recrystallization from methanol, while use of carbon in the recrystallization offers additional control of product color. Typical yield from tetralone to recrystallized hydrochloric acid salt of racemic N-methyl-4(3,4-dichlorophenyl)-1,2,3,4-tetrahydro-1-naphthalenamine is 85%. Alternatively, the ethanol solution of racemic free base is distilled under vacuum to remove monomethylamine, with ethanol being essentially replaced by tetrahydrofuran. Hydrochloric acid (35%, 21.5 g, 1 mol. eq) is added and racemic sertraline hydrochloride isolated by filtration as described above in ethanol. Overall purity can be enhanced by recrystallization from methanol, while use of carbon in the recrystallization hydrochloric acid salt of racemic sertraline is approximately 85%.

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention.

What is claimed is:

1. A process for preparing N-[4-(3,4-dichlorophenyl)-3,4-dihydro-1(2H)-napthalenylidene]methaneamine, depicted below,

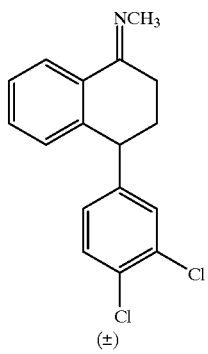

II (±)

comprising reacting 4-(3,4-dichlorophenyl)-3,4-dihydro-1(2H)-napthalenone, depicted below,

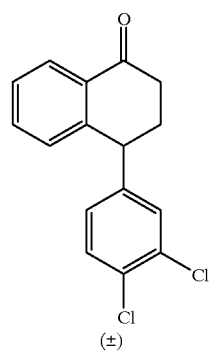

I (±)

with monomethylamine in an alcohol solvent having a boiling point, under reaction conditions, that is greater than about 55° C., and in which monomethylamine is soluble.

2. A process according to claim 1, wherein the ketimine product of formula II that is formed in such reaction is hydrogenated to form a mixture of racemic cis sertraline and racemic trans sertraline.

3. A process for preparing the optically pure (+) enantiomer of N-[4-(3,4-dichlorophenyl)-3,4-dihydro-1(2H)-napthalenylidene]methaneamine, depicted below,

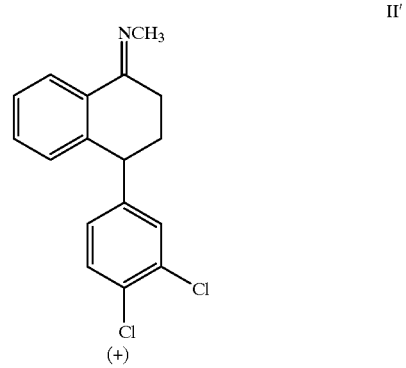

II'

(+)

or an optically enriched (+) mixture of the (+) and (−) enantiomers of the same, respectively; comprising reacting the optically pure (+) enantiomer 4-(3,4-dichlorophenyl)-3,4-dihydro-1(2H)-napthalenone, depicted below,

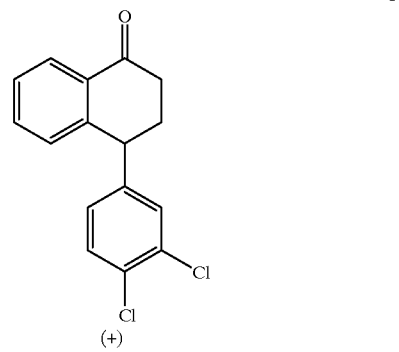

I'

(+)

or an optically enriched (+) mixture of the (+) and (−) enantiomers of the same, respectively, with monomethylamine in an alcohol solvent having a boiling point, under reaction conditions, that is greater than about 55° C., and in which monomethylamine is soluble.

4. A process according to claim 3, wherein the optically pure or optically enriched (+) ketimine product of formula II' or an optically enriched (+) mixture of the (+) and (−) enantiomers of the same, that is formed in such reaction is hydrogenated to form an optically pure (+) mixture of cis (+) sertraline and trans (+) sertraline, or an optically enriched (+) mixture of cis (+) sertraline, trans (+) sertraline, cis (−) sertraline and trans (−) sertraline.

5. A process according to claim 1 wherein an excess of monomethylamine with respect to the 4-(3,4-dichlorophenyl)-3,4-dihydro-1(2H)-napthalenone starting material is employed.

6. A process according to claim 1 wherein the reaction is conducted at a temperature in the range of about 50° C. to about 120° C., and a pressure in the range of about atmospheric pressure to about 100 psig.

7. A process according to claim 1 wherein the solvent is methanol.

8. A process according to claim 1 wherein the solvent is isopropanol.

9. A process according to claim 1 wherein the solvent is n-propanol.

10. A process according to claim 1 wherein the solvent is ethanol.

11. A process according to claim 2 wherein the ketimine product of formula II is hydrogenated in situ in the same alcohol in which it was formed to yield a mixture of racemic cis sertraline and racemic trans sertraline.

12. A process according to claim 3 wherein an excess of monomethylamine with respect to the optically active 4-(3,4-dichlorophenyl)-3,4-dihydro-1(2H)-napthalenone starting material is employed.

13. A process according to claim 3 wherein the reaction is conducted at a temperature in the range of about 50° C. to about 120° C., and a pressure in the range of about atmospheric pressure to about 100 psig.

14. A process according to claim 3 wherein the solvent is methanol.

15. A process according to claim 3 wherein the solvent is isopropanol.

16. A process according to claim 3 wherein the solvent is n-propanol.

17. A process according to claim 3 wherein the solvent is ethanol.

18. A process according to claim 4 wherein the ketimine product of formula II' is hydrogenated in situ in the same alcohol in which it was formed to yield an optically pure mixture of cis (+) sertraline and trans (+) sertraline, or an optically enriched (+) mixture of cis (+) sertraline, cis (−) sertraline, trans (+) sertraline and trans (−) sertraline.

19. A process for preparing a mixture of racemic cis sertraline and racemic trans sertraline, comprising reacting a compound of the formula I, as depicted in claim 1, with monomethylamine, hydrogen gas, and a hydrogenation catalyst in an alcohol solvent having a boiling point, under reaction conditions, that is greater than about 55° C., and in which monomethylamine is soluble.

20. A process for preparing an optically pure (+) mixture of cis (+) sertraline and trans (+) sertraline, or an optically enriched (+) mixture of cis (+) sertraline, trans (+) sertraline, cis (−) sertraline and trans (−) sertraline, comprising reacting a compound of the formula I', as depicted in claim 3, with monomethylamine, hydrogen gas, and a hydrogenation catalyst in an alcohol solvent having a boiling point, under reaction conditions, that is greater than about in which monomethylamine is soluble.

21. The process of claim 1, wherein the alcohol solvent comprises an alkanol or a mixture of two or more alkanols.

22. The process of claim 21, wherein the alkanol is selected from primary, secondary and tertiary straight or branched $(C_1-C_6)$alkanols.

23. The process of claim 3, wherein the alcohol solvent comprises an alkanol or a mixture of two or more alkanols.

24. The process of claim 23, wherein the alkanol is selected from primary, secondary and tertiary straight or branched $(C_1-C_6)$alkanols.

25. A process according to claim 22, wherein the solvent is selected from methanol, ethanol, n-propanol, isopropanol, n-butanol, t-butanol, isobutanol and benzylalcohol.

26. A process according to claim 24, wherein the solvent is selected from methanol, ethanol, n-propanol, isopropanol, n-butanol, t-butanol, isobutanol, and benzylalcohol.

27. The process of claim 19, wherein the alcohol solvent comprises an alkanol or a mixture of two or more alkanols.

28. The process of claim 27, wherein the alkanol is selected from primary, secondary and tertiary straight or branched $(C_1-C_6)$alkanols.

29. The process of claim 20, wherein the alcohol solvent comprises an alkanol or a mixture of two or more alkanols.

30. The process of claim 29, wherein the alkanol is selected from primary, secondary and tertiary straight or branched $(C_1-C_6)$alkanols.

* * * * *